US011237158B2

(12) United States Patent
Xu et al.

(10) Patent No.: US 11,237,158 B2
(45) Date of Patent: Feb. 1, 2022

(54) TIME-RESOLVED FLUORESCENT IMMUNOCHROMATOGRAPHIC TEST STRIP FOR DETECTING PACLITAXEL DRUGS AS WELL AS PREPARATION METHOD AND APPLICATION THEREOF

(71) Applicant: BEIJING DIAGREAT BIOTECHONOLOGIES CO., LTD., Beijing (CN)

(72) Inventors: Xiuli Xu, Beijing (CN); Yanxin Wang, Beijing (CN); Yuanrong Chang, Beijing (CN); Jianping Zhou, Beijing (CN)

(73) Assignee: Beijing Diagreat Biotechnologies Co., Ltd., Beijing (CN)

( * ) Notice: Subject to any disclaimer, the term of this patent is extended or adjusted under 35 U.S.C. 154(b) by 117 days.

(21) Appl. No.: 16/458,972

(22) Filed: Jul. 1, 2019

(65) Prior Publication Data
US 2020/0209232 A1   Jul. 2, 2020

(30) Foreign Application Priority Data

Dec. 26, 2018   (CN) .......................... 201811600900.4

(51) Int. Cl.
| | | |
|---|---|---|
| G01N 33/543 | (2006.01) | |
| G01N 33/533 | (2006.01) | |
| G01N 33/53 | (2006.01) | |
| G01N 21/64 | (2006.01) | |
| G01N 21/84 | (2006.01) | |

(52) U.S. Cl.
CPC ... *G01N 33/54366* (2013.01); *G01N 21/6428* (2013.01); *G01N 21/8483* (2013.01); *G01N 33/533* (2013.01); *G01N 33/5308* (2013.01); *G01N 2407/02* (2013.01); *G01N 2458/10* (2013.01); *G01N 2800/52* (2013.01)

(58) Field of Classification Search
CPC .......... G01N 21/6428; G01N 21/8483; G01N 2407/02; G01N 2458/10; G01N 2800/52; G01N 33/5308; G01N 33/533; G01N 33/54366; G01N 33/558; G01N 33/577; G01N 33/94
See application file for complete search history.

(56) References Cited

U.S. PATENT DOCUMENTS

| | | | |
|---|---|---|---|
| 2009/0215993 A1 | 8/2009 | Ghoshal et al. | |
| 2015/0285827 A1* | 10/2015 | Lee ........................ | G01N 33/94 436/501 |

FOREIGN PATENT DOCUMENTS

| | | |
|---|---|---|
| CN | 103884843 A | 6/2014 |
| CN | 108732344 A | 11/2018 |
| CN | 109061152 A | 12/2018 |

OTHER PUBLICATIONS

Edwards et al., "The remarkable flexibility of the human antibody repertoire; isolation of over one thousand different antibodies to a single protein, Blys," J. Mol. Biol., 2003, vol. 334, pp. 103-118.*
Juntunen et al., "Performance of fluorescent europium(III) nanoparticles and colloidal gold reporters in lateral flow bioaffinity assay," Anal. Biochem., 2012, vol. 428, issue 1, pp. 31-38.*
Cui et al., "Development of a Competitive Time-Resolved Fluoroimmunoassay for Paclitaxel," Phytochem Anal, 2018, vol. 29, No. 3, pp. 284-289; Epub Dec. 20, 2017.*
Chao et al., "Development of an indirect competitive enzyme-linked immunosorbent assay (icELISA) using highly specific monoclonal antibody against paclitaxel," J. Nat. Med., 2013 vol. 67, No. 3, pp. 512-518.*
A printout "Phosphate-buffered saline (PBS, 10X), with Triton® X-100" retrieved from https://www.alfa.com/en/catalog/J63521/ on May 4, 2021.*
Zhang et al., "Monoclonal antibody—europium conjugate-based lateral flow time-resolved fluoroimmunoassay for quantitative determination of T-2 toxin in cereals and feed," Anal. Methods, 2015, vol. 7, pp. 2822-2829.*
First Office Action, dated Dec. 13, 2019, 9 pages, issued in Chinese Application No. 201811600900.4.
Second Office Action, dated Mar. 2, 2020, 11 pages, issued in Chinese Application No. 201811600900.4.
Third Office Action, dated May 18, 2020, 10 pages, issued in Chinese Application No. 201811600900.4.

* cited by examiner

*Primary Examiner* — Galina M. Yakovleva
(74) *Attorney, Agent, or Firm* — Avant Law Group, LLC

(57) ABSTRACT

Some embodiments of the disclosure provide a time-resolved fluorescent immunochromatographic test strip for detecting paclitaxel drugs as well as a preparation method and application thereof. In some embodiments, the test strip includes a test paper and a sample diluent. The test paper includes a bottom plate, a sample absorption pad, a fluorescent microsphere pad, a bonding pad, and an absorbent pad. The sample absorption pad, the fluorescent microsphere pad, the bonding pad, and the absorbent pad are sequentially overlapped on the bottom plate. The fluorescent microsphere pad is sprayed with a fluorescent microsphere-labeled anti-paclitaxel monoclonal antibody. A detection area and a quality control area are immobilized on the bonding pad. The detection area is sprayed with a paclitaxel hapten-carrier protein conjugate. The quality control area is sprayed with a goat anti mouse antibody.

5 Claims, 1 Drawing Sheet

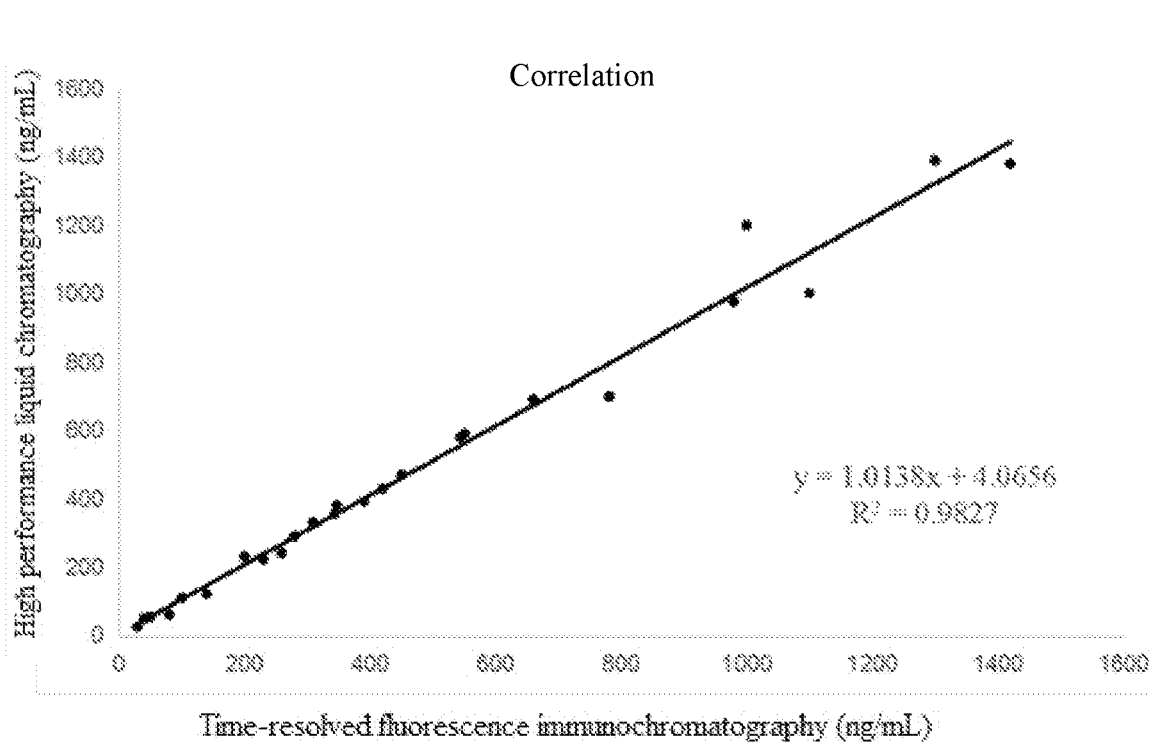

TIME-RESOLVED FLUORESCENT IMMUNOCHROMATOGRAPHIC TEST STRIP FOR DETECTING PACLITAXEL DRUGS AS WELL AS PREPARATION METHOD AND APPLICATION THEREOF

CROSS REFERENCE TO RELATED APPLICATIONS

This application claims priority to Chinese application number 20181160090-0.4 filed Dec. 26, 2018, the disclosure of which is incorporated by reference herein in its entirety.

FIELD OF THE DISCLOSURE

The disclosure relates generally to the field of in vitro diagnostic reagents. More specifically, the disclosure relates to the field of a time-resolved fluorescent immunochromatographic test strip for detecting paclitaxel drugs as well as a preparation method and application thereof.

BACKGROUND

The structural formula of Paclitaxel (PTX) is shown in following formula II:

Formula II

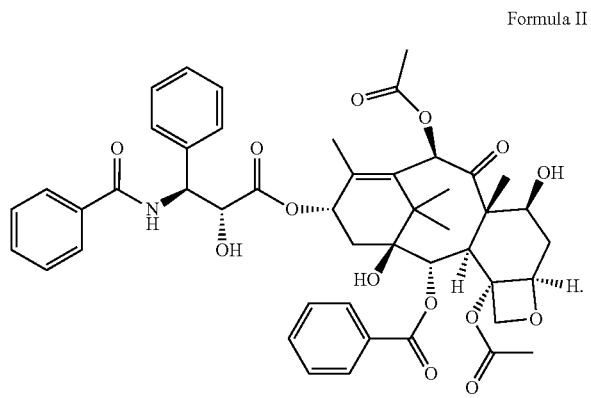

PTX is a tricyclic diterpene compound isolated from the taxus plants, and has a unique anti-tumor mechanism that induces tubulin polymerization and inhibits cell division. PTX has been approved by the U.S. Food and Drug Administration (FDA) as a new drug against advanced cancers in 1992 and is still the initial clinical drug for breast cancer, uterine cancer, ovarian cancer and other cancers. Due to the increasing market demand for PTX, the main raw material, i.e., taxus chinensis for the production of PTX is a scarce resource, and the content thereof in plants is extremely low, the medical value and research value of PTX have great upside potential.

In clinical therapy, PTX has side effects such as decreased bone marrow density, allergic reaction, neutropenia, hypotension, bradycardia, nausea, and emesis, and the therapeutic effect is highly correlated with its blood concentration. However, due to the nonlinear pharmacokinetic characteristics of PTX and the individualized differences of the body, the efficacy of PTX is difficult to grasp, and the occurrence of adverse reactions is also difficult to control. At present, the results of the study on the pharmacokinetics of PTX are not uniform enough. Therefore, it is necessary to carry out blood concentration monitoring and individualized pharmacokinetic studies of PTX.

At present, methods for monitoring the concentrations of PTX drugs at home and abroad include Thin Layer Chromatography (TLC), Capillary Electrophoresis (CE), High Performance Liquid Chromatography (HPLC), and biochemical methods. However, the methods are not suitable for large-scale clinical promotion. Although the Turbidimetric Inhibition Immunoassay (TIA) is available on the market for the determination of PTX, the sensitivity is low and the cost is high, which cannot meet the ever-increasing clinical monitoring needs.

At present, there is a lack of sensitive and specific PTX detection reagents on the market. Therefore, research and development of high-quality, low-cost, and simple-use PTX detection reagents have become an urgent need for clinical detection.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

Some embodiments of the disclosure provide a time-resolved fluorescent immunochromatographic test strip for detecting PTX drugs with high detection sensitivity, high specificity, low production cost, and simple use.

In some embodiments, a time-resolved fluorescent immunochromatographic test strip for detecting paclitaxel drugs includes a test paper and a sample diluent. The test paper includes a bottom plate and a sample absorption pad, a fluorescent microsphere pad, a bonding pad and an absorbent pad which are sequentially overlapped on the bottom plate, the fluorescent microsphere pad is sprayed with a fluorescent microsphere-labeled anti-paclitaxel monoclonal antibody, a detection area and a quality control area are immobilized on the bonding pad, the detection area is sprayed with a paclitaxel hapten-carrier protein conjugate, and the quality control area is sprayed with a goat anti mouse antibody. The anti-paclitaxel monoclonal antibody is prepared by using a paclitaxel hapten-carrier protein conjugate as an immunogen, the paclitaxel hapten-carrier protein conjugate is obtained by coupling a 7-xylosyl paclitaxel hapten with a carrier protein, and the molecular structural formula thereof is shown in the following formula I:

Formula I

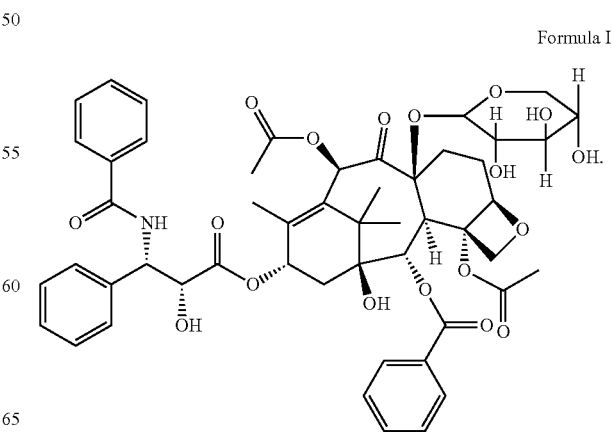

Optionally, the fluorescent microsphere includes rare earth ions Eu+ coated with polystyrene, and the surface of the microsphere contains a carboxyl group.

Optionally, the diameter of the fluorescent microsphere is 100-300 nm.

Optionally, the sample diluent is 0.008-0.012 mol/L of PB buffer, the pH of the PB buffer is 7.2-7.6, and the PB buffer contains 0.15-0.25% (W/V) of Triton x-100.

In other embodiments, a preparation method of the above-described time-resolved fluorescent immunochromatographic test strip includes a preparation method of a sample absorption pad, a preparation method of a fluorescent microsphere pad, a preparation method of a bonding pad, and assembly and shearing of the sample absorption pad, the fluorescent microsphere pad, the bonding pad, and an absorbent pad.

Optionally, the preparation method of the sample absorption pad includes the steps of: (1) soaking a glass fiber membrane with 0.08-0.12 mol/L of phosphate buffer with the pH 7.0-7.4 for 1.5-3 h; and (2) drying at 37° C. for 1.5-3 h, the phosphate buffer containing 0.4-0.6% by volume of bovine serum albumin.

Optionally, the preparation method of the fluorescent microsphere pad includes the steps of: (1) labeling an anti-paclitaxel monoclonal antibody with a fluorescent microsphere to obtain a labeled antibody; (2) diluting the labeled antibody with a storage buffer to obtain 5-20 μg/ml labeled antibody diluent; and (3) spraying the labeled antibody diluent onto the glass fiber membrane at a quantity of 1-6 μl/cm, and drying at 37° C. for 12-18 h to obtain a fluorescent microsphere pad.

Optionally, the storage buffer is 0.008-0.012 mol/L of PB buffer, the pH of the PB buffer is 7.2-7.6, and the PB buffer contains 0.008-0.012% (W/V) of NaN3 and 0.08-0.12% of bovine serum albumin.

Optionally, the preparation method of the bonding pad includes the steps of: (1) defining a detection area and a quality control area on a nitrocellulose membrane; (2) diluting a paclitaxel hapten-carrier protein conjugate with 0.04-0.06 mol/L of PB buffer with the pH of 7.0-7.4 to obtain 160-240 μg/ml of conjugate diluent, and spraying the conjugate diluent onto the detection area of the nitrocellulose membrane at the quantity of 1-1.5 μL/cm; (3) diluting a goat anti mouse antibody with 0.04-0.06 mol/L of PB buffer with the pH of 7.0-7.4 to obtain 160-240 μg/ml of goat anti mouse antibody diluent, and spraying the goat anti mouse antibody diluent onto the quality control area of the nitrocellulose membrane at the quantity of 1-1.5 μL/cm; and (4) drying the sprayed nitrocellulose membrane at 37° C. for 4-6 h to obtain a bonding pad. Optionally, the steps (2) and (3) are not chronologically defined.

In further embodiments, an application of the above-described time-resolved fluorescent immunochromatographic test strip, or the time-resolved fluorescent immunochromatographic test strip prepared by the above-described preparation method in detection of paclitaxel drugs includes the steps of: (1) pre-treating a sample with the sample diluent to obtain a sample to be tested; (2) detecting the sample to be tested by using the time-resolved fluorescent immunochromatographic test strip to obtain a detected test strip; and (3) analyzing the detected test strip by a fluorescence detection analyzer to obtain a test result.

BRIEF DESCRIPTION OF THE DRAWINGS

The FIGURE is a correlation curve chart of two detection methods according to Embodiment 4 of the disclosure.

DETAILED DESCRIPTION

Some embodiments of the disclosure provide a time-resolved fluorescent immunochromatographic test strip for detecting PTX drugs, including a test paper and a sample diluent, the test paper including a bottom plate and a sample absorption pad, a fluorescent microsphere pad, a bonding pad and an absorbent pad which are sequentially overlapped on the bottom plate. The fluorescent microsphere pad is sprayed with a fluorescent microsphere-labeled anti-PTX monoclonal antibody, a detection area and a quality control area are immobilized on the bonding pad, the detection area is sprayed with a PTX hapten-carrier protein conjugate, and the quality control area is sprayed with a goat anti mouse antibody. The anti-PTX monoclonal antibody is prepared by using a PTX hapten-carrier protein conjugate as an immunogen, the PTX hapten-carrier protein conjugate is obtained by coupling a 7-xylosyl PTX hapten with a carrier protein, and the molecular structural formula is shown in the following formula I:

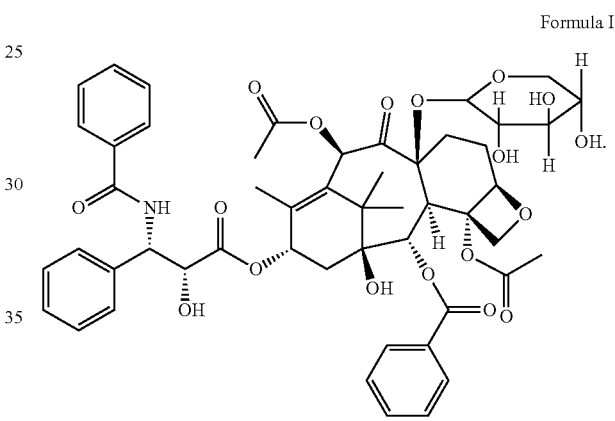

Formula I

The test strip provided by the disclosure may include a sample diluent. The sample diluent may be a PB buffer. The concentration of the PB buffer may be 0.008-0.012 mol/L and preferably 0.01 mol/L, and the pH of the PB buffer may be 7.2-7.6 and preferably 7.4. The PB buffer may contain Triton x-100, and the weight/volume fraction (W/V) of the Triton x-100 may be 0.15-0.25% and preferably 0.2%.

The test strip provided by the disclosure may include a test paper. The test paper may include a bottom plate and a sample absorption pad, a fluorescent microsphere pad, a bonding pad and an absorbent pad which are sequentially overlapped on the bottom plate.

In the disclosure, the bottom plate may be a PVC bottom plate. The PVC bottom plate may have stable chromatogram, no fluorescent substance, and/or high bonding strength.

In the disclosure, a preparation method for the sample absorption pad may include the steps of soaking a glass fiber membrane with a phosphate buffer and drying same. In the disclosure, the concentration of the phosphate buffer may be 0.08-0.12 mol/L and preferably 0.1 mol/L, and the pH of the phosphate buffer may be 7.0-7.4 and preferably 7.2. The phosphate buffer may contain bovine serum albumin, and the volume percentage of the bovine serum albumin may be 0.4-0.6% and preferably 0.5%. The soaking time may be 1.5-3 h and preferably 2 h. The drying temperature may be 37° C. The drying time may be 1.5-3 h and preferably 2 h.

In the disclosure, a preparation method for the fluorescent microsphere pad may include the steps of: (1) an anti-PTX monoclonal antibody is labeled with a fluorescent microsphere to obtain a labeled antibody; (2) the labeled antibody is diluted with a storage buffer to obtain 5-20 µg/mL labeled antibody diluent; and (3) the labeled antibody diluent is sprayed onto the glass fiber membrane at a quantity of 1-6 µl/cm, and dried at 37° C. for 12-18 h to obtain a fluorescent microsphere pad.

In other embodiments, the disclosure may first label an anti-PTX monoclonal antibody with a fluorescent microsphere to obtain a labeled antibody. The fluorescent microsphere may be a microsphere including rare earth ions Eu+ coated with polystyrene, and the surface of the microsphere contains a carboxyl group. The diameter of the fluorescent microsphere may be 100-300 nm and preferably 150-250 nm. The anti-PTX monoclonal antibody is prepared by using a PTX hapten-carrier protein conjugate as an immunogen, the PTX hapten-carrier protein conjugate is obtained by coupling a 7-xylosyl PTX hapten with a carrier protein, and the molecular structural formula thereof is formula I.

After the labeled antibody is obtained, the disclosure dilutes the labeled antibody with a storage buffer to obtain a labeled antibody diluent. In the disclosure, the storage buffer may be the PB buffer. The concentration of the PB buffer may be 0.008-0.012 mol/L and preferably 0.01 mol/L of the PB buffer. The pH of the PB buffer may be 7.2-7.6 and preferably 7.4. The PB buffer may contain NaN3 and bovine serum albumin, and the W/V of the NaN3 may be 0.008-0.012% and preferably 0.01%, and the volume fraction of the bovine serum albumin may be 0.08-0.12% and preferably 0.1%. In the disclosure, the concentration of the labeled antibody diluent may be 5-20 µg/mL and preferably 10 µg/mL.

After the labeled antibody diluent is obtained, the disclosure sprays the labeled antibody diluent onto the glass fiber membrane. In the disclosure, the quantity for spray may be 1-6 µl/cm and preferably 3 µl/cm. Drying is performed after spraying, the drying temperature may be 37° C., and the drying time may be 12-18 h and preferably 15 h. The fluorescent microsphere pad is obtained after drying.

In further embodiments, a preparation method for the bonding pad may include the following steps. (1) A detection area and a quality control area is defined on a nitrocellulose membrane. (2) A PTX hapten-carrier protein conjugate is diluted with 0.04-0.06 mol/L of PB buffer with the pH of 7.0-7.4 to obtain 160-240 µg/ml of conjugate diluent, and the conjugate diluent is sprayed onto the detection area of the nitrocellulose membrane at the quantity of 1-1.5 µL/cm. (3) A goat anti mouse antibody is diluted with 0.04-0.06 mol/L of PB buffer with the pH of 7.0-7.4 to obtain 160-240 µg/ml of goat anti mouse antibody diluent, and the goat anti mouse antibody diluent is sprayed onto the quality control area of the nitrocellulose membrane at the quantity of 1-1.5 µL/cm. (4) The sprayed nitrocellulose membrane is dried at 37° C. for 4-6 h to obtain a bonding pad. The steps (2) and (3) may or may not chronologically defined.

According to an embodiment, the disclosure first defines a detection area and a quality control area on a nitrocellulose membrane, the detection area is sprayed with a PTX hapten-carrier protein conjugate, and the quality control area is sprayed with a goat anti mouse antibody.

According to another embodiment, the PTX hapten-carrier protein conjugate may be diluted with a PB buffer. In the disclosure, the concentration of the PB buffer may be 0.04-0.06 mol/L and preferably 0.05 mol/L. The pH of the PB buffer may be 7.0-7.4 and preferably 7.2. A conjugate diluent is obtained after dilution. The concentration of the conjugate diluent may be 160-240 µg/ml and preferably 200 µg/ml. After the conjugate diluent is obtained, the disclosure preferably sprays the conjugate diluent onto the detection area of the nitrocellulose membrane, and the quality for spray may be 1-1.5 µL/cm and preferably 1.2 µL/cm.

According to a further embodiment, the goat anti mouse antibody may be diluted with a PB buffer. In the disclosure, the concentration of the PB buffer may be 0.04-0.06 mol/L and preferably 0.05 mol/L. The pH of the PB buffer may be 7.0-7.4 and preferably 7.2. A goat anti mouse antibody diluent is obtained after dilution. The concentration of the goat anti mouse antibody diluent may be 160-240 µg/ml and preferably 200 µg/ml. After the goat anti mouse antibody diluent is obtained, the disclosure preferably sprays the goat anti mouse antibody diluent onto the quality control area of the nitrocellulose membrane, and the quality for spray may be 1-1.5 µL/cm and preferably 1.2 µL/cm.

The spraying sequence of the detection area and the quality control area is not limited in the disclosure. After the spraying is finished, the disclosure optionally dries the sprayed nitrocellulose membrane at 37° C., and the drying time may be 4-6 h and optionally 5 h. A bonding pad is obtained after drying.

In the disclosure, the absorbent pad may be a pure white absorbent paper prepared from pure plant fibers. The absorbent paper has suitable thickness, high water absorption capacity, and medium water absorption speed, etc. The disclosure provides a preparation method of the time-resolved fluorescent immunochromatographic test strip, including a preparation method of a sample absorption pad, a preparation method of a fluorescent microsphere pad, a preparation method of a bonding pad, and assembly and shearing of the sample absorption pad, the fluorescent microsphere pad, the bonding pad, and an absorbent pad. In the disclosure, the preparation method of the sample absorption pad, the preparation method of the fluorescent microsphere pad, and the preparation method of the bonding pad are as described above.

In the disclosure, the sample absorption pad, the fluorescent microsphere pad, the bonding pad, and the absorbent pad may be sequentially overlapped on the bottom plate, and then the pasted plate is cut into test strips as needed. The width of the test strip is not particularly limited in the disclosure, and the widths conventionally set in the art as needed are applicable.

In some embodiments, the disclosure also provides an application of the time-resolved fluorescent immunochromatographic test strip in detection of PTX drugs, including the steps of: (1) pre-treating a sample with the sample diluent to obtain a sample to be tested; (2) detecting the sample to be tested by using the time-resolved fluorescent immunochromatographic test strip to obtain a detected test strip; and (3) analyzing the detected test strip by a fluorescence detection analyzer to obtain a test result.

In the disclosure, the detection temperature of the sample diluent may be 20-25° C., and the detection time may be 15 min. After the test is completed, the disclosure may obtain the ratio of the time-resolved fluorescent intensity of the detection area on the test strip to the time-resolved fluorescent intensity of the quality control area with an instrument. Based on a relationship curve of the ratio of the time-resolved fluorescent intensity of the detection area on the pre-built test strip to the time-resolved fluorescent intensity of the quality control area and the concentration of PTX drugs, the content of PTX drug in the sample to be tested is obtained, and finally, the content of the PTX drug in the sample to be tested is obtained by conversion. If the fluorescence signal intensity is not detected in the quality control area, it is indicated that the operation process is incorrect or the test strip is expired.

The following describes multiple exemplary embodiments of the time-resolved fluorescent immunochromatographic test strip for detecting PTX drugs as well as the preparation method and application thereof.

Embodiment 1

1. Synthesis and Identification of the PTX Hapten-Carrier Protein Conjugate

PTX is a small molecular substance which is only immunoreactive, has no immunogenicity, and cannot induce an immune response in the body. 7-Xylosyltaxol is an analog of PTX which is immunogenic directly by coupling an o-phenolic hydroxy of 7-xylosyltaxol to a carrier protein.

(1) Preparation of a 7-Xylosyltaxol-BSA Immunogen 0.5 mL of methanol solution in which 5 mg of 7-xylosyltaxol is dissolved is added in 1 ml of 10 mg/mL NaIO4 solution. The reaction is carried out by stirring at room temperature for 1 h in the dark. The reaction mixture is added to 1 ml of 5 mg/mL BSA solution (50 mmol/L carbonate buffer with the pH of 9.6), adjusted to pH 9 with 1 mol/L Na2CO3 solution, stirred for 12 h, and dialyzed against water for 5 times, and stored at 20° C. for future use.

(2) Preparation of a 7-Xylosyltaxol-OVA Coating Antigen 0.5 mL of methanol solution in which 3 mg of 7-xylosyltaxol is dissolved is added to 1 ml of 10 mg/mL NaIO4, and the reaction is carried out by stirring at room temperature for 1 h in the dark. The reaction mixture is added to 1 ml of 5 mg/mL OVA solution (50 mmol/L carbonate buffer with the pH of 9.6), adjusted to pH 9 with 1 mol/L Na2CO3 solution, stirred for 12 h, and dialyzed against water for 5 times, and stored at 20° C. for future use.

Identification of a PTX Hapten-Carrier Protein Conjugate

Molecular weight analysis of four proteins, i.e., BSA, 7-xylosyltaxol-BSA, OVA, and 7-xylosyltaxol-OVA, is performed by Native SDS-PAGE. The results show that the molecular weight of 7-xylosyltaxol-BSA is significantly greater than that of BSA, and the molecular weight of 7-xylosyltaxol-OVA is significantly greater than that of OVA, indicating that 7-xylosyltaxol is successfully coupled to BSA and OVA.

2. Preparation of PTX Monoclonal Antibody

The prepared 7-xylosyltaxol-BSA immunogen is immunized with Balb/c by a conventional method, and the Balb/c mouse spleen cells which produce specific antibodies are fused with myeloma cells SP20 after booster immunization, and an indirect competitive enzyme-linked immunoassay method is used to assay cell supernatant, and positive wells are screened. The positive wells are cloned by using a limiting dilution method to obtain and establish a monoclonal antibody-producing hybridoma cell line.

Balb/c mice (8 weeks old) are intraperitoneally injected with sterile paraffin oil, and hybridoma cells are intraperitoneally injected 7-14 days later, and ascites is collected 7-10 days later. The ascites is purified by the octanoic acid-saturated ammonium sulfate method, the purity is identified by SDS-PAGE electrophoresis, and storage is carried out at −20° C.

3. Preparation of a Fluorescent Microsphere-Labeled PTX Monoclonal Antibody (1) Activation: 100 uL of commercially available microsphere suspension internally embedded with a fluorescent dye and modified with a carboxyl functional group at the surface is suspended in 400 uL of activation buffer (50 mmol/L MES with the pH of 6.0), and 0.5 mg of EDC and 0.5 mg of NHS are added, and the mixture is shaken and activated at room temperature for 15 min after mixing.

(2) Coupling: the suspension of (1) is centrifuged at 4° C., 10,000 r/min for 10 min, the supernatant is discarded, re-suspension is carried out in the activation buffer, 20 ug of PTX monoclonal antibody solution is added, and the mixture is shaken and coupled at room temperature for 120 min after mixing.

(3) Blocking: the suspension of (2) is added to 100 ul of 10% BSA solution, and the mixture is shaken and blocked overnight at room temperature after mixing.

(4) Storage: the suspension of (3) is centrifuged at 4° C., 10,000 r/min for 10 min, the supernatant is discarded, and re-suspension is carried out in a storage buffer (a PB buffer containing 0.01% NaN3 and 0.1% BSA with the pH of 7.4), the microspheres are washed once, and the mixture is stored at 4° C. in the dark after mixing.

(5) Preparation of a glass fiber pad

The stored fluorescent microsphere-labeled PTX monoclonal antibody is diluted to 10 μg/mL in the storage buffer, and then sprayed with a gold-standard film sprayer with the quantity of 3 μL/cm, dried at 37° C. for 15 h, and taken out and sealed for storage.

(6) Preparation of a nitrocellulose (NC) membrane

The PTX hapten-OVA conjugate is diluted to 200 ug/mL with 0.05 mol/L of PB buffer with the pH of 7.2, and sprayed on the detection area (T) of the NC membrane with the gold-standard film sprayer with the quantity of 1.2 uL/cm. The goat anti mouse antibody is diluted to 200 ug/mL with 0.05 mol/L of PB buffer with the pH of 7.2, and sprayed onto the detection area (C) of the NC membrane with the gold-standard film sprayer with the quality for spray of 1.2 uL/cm, and dried at 37° C. for 5 h for future use.

(7) Preparation of a sample absorption pad

The sample absorption pad is soaked in 0.1 mol/L of phosphate buffer with the pH of 7.2 containing 0.5% bovine serum albumin (volume fraction) for 2 h, and dried at 37° C. for 2 h for future use.

(8) Assembly of a test strip

The sample absorption pad, the glass fiber pad, the NC membrane, and the absorbent pad are sequentially overlapped and immobilized from left to right on the bottom plate, the end of the sample absorption pad is connected to the beginning of the glass fiber pad, the end of the glass fiber pad is connected to the beginning of the NC membrane, the end of the NC membrane is connected to the beginning of the absorbent pad, the beginning of the sample absorption pad is aligned with the beginning of the bottom plate, and the end of the absorbent pad is aligned with the end of the bottom plate, and then cut into a small strip with a width of 3.96 mm by a machine to be packed in special plastic cards to form a test strip.

Embodiment 2

An application of the time-resolved fluorescent immunochromatographic test strip for detecting PTX drugs.

1. Sample Pretreatment 20 ul of sample is accurately pipetted into 180 ul of sample diluent and mixed fully.

2. Detection with the Test Strip 80 uL of sample solution to be tested is accurately pipetted into a test strip loading well with a micropipette, and reaction is carried out at room temperature (20-25° C.) for 15 min. The test strip is inserted into a load carrier of a fluorescence detector, an item to be tested is selected by touching a display screen, a "Detection Start" button is pressed, the fluorescence detector automatically scans the test strip, and a test result is read through the display screen of an instrument or printed.

3. Analysis of Test Results

Quantitative detection: after the test is completed, the instrument obtains the ratio of the time-resolved fluorescent intensity of the detection area on the test strip to the time-resolved fluorescent intensity of the quality control area. Based on a relationship curve of the ratio of the time-resolved fluorescent intensity of the detection area on the pre-built test strip to the time-resolved fluorescent intensity of the quality control area and the concentration of PTX drugs, the content of PTX drug in the sample to be tested is obtained, and finally, the content of the PTX drug in the sample to be tested is obtained by conversion.

Expiration: if the fluorescence signal intensity is not detected in the quality control area, it is indicated that the operation process is incorrect or the test strip is expired.

Embodiment 3

The cross reaction rate is measured according to the method of Embodiment 2.

Several analogs of PTX are selected for interference testing. The results are shown in Table 1.

TABLE 1

PTX analog interference test results

| Compound name | Test concentration | Cross reaction rate |
|---|---|---|
| Paclitaxel | 100 ng/mL | 100% |
| Docetaxel | 1,000 ng/mL | <1% |
| 7-Xylosyltaxol | 1,000 ng/mL | <1% |
| Cephalomannine | 1,000 ng/mL | <0.04% |
| Baccatin III | 1,000 ng/mL | <0.01% |
| 10-Deacetyl-baccatin III | 1,000 ng/mL | <0.01% |
| 1-Hydroxybaccatin I | 1,000 ng/mL | <0.01% |
| 13-Acetyl-9-dihydrobaccatin III | 1,000 ng/mL | <0.01% |
| 1-Acetoxyl-5-deacetyl-baccatin I | 1,000 ng/mL | <0.01% |

The results in Table 1 indicate that the PTX test strip of the disclosure has high specificity and has no cross reaction to several PTX analogs.

Embodiment 4

Correlation analysis: the PTX-based time-resolved fluorescent immunochromatographic test strip provided by the disclosure is used to detect the content of PTX in human serum according to the method of Embodiment 2. The detection results are compared with the results of HPLC for assay of the content of PTX in human serum. The results are shown in Table 2.

TABLE 2

Statistical results of two methods for detecting the content of PTX in human serum

| Sample No. | Fluorescent immunochromatography (ng/mL) | High performance liquid chromatography (ng/mL) |
|---|---|---|
| Sample 1 | 30 | 26 |
| Sample 2 | 40 | 50 |
| Sample 3 | 50 | 55 |
| Sample 4 | 80 | 60 |
| Sample 5 | 100 | 110 |
| Sample 6 | 140 | 122 |
| Sample 7 | 200 | 230 |
| Sample 8 | 259 | 241 |
| Sample 9 | 280 | 290 |
| Sample 10 | 310 | 330 |
| Sample 11 | 450 | 470 |
| Sample 12 | 230 | 222 |
| Sample 13 | 344 | 356 |
| Sample 14 | 420 | 430 |
| Sample 15 | 550 | 590 |
| Sample 16 | 660 | 690 |
| Sample 17 | 781 | 700 |
| Sample 18 | 1000 | 1200 |
| Sample 19 | 1100 | 1001 |
| Sample 20 | 980 | 977 |
| Sample 21 | 1420 | 1380 |
| Sample 22 | 1300 | 1390 |
| Sample 23 | 347 | 380 |
| Sample 24 | 390 | 392 |
| Sample 25 | 544 | 580 |

The above statistical results are made into a correlation curve chart in the FIGURE. According to the results shown in the FIGURE, the PTX-based time-resolved fluorescent immunochromatographic test strip provided by the disclosure has high correlation between the content of PTX in human serum and the HPLC, and the correlation coefficient is r=0.991, indicating that the PTX-based time-resolved fluorescent immunochromatographic test strip provided by the disclosure has accurate and reliable measurement results, thereby meeting the clinical needs.

Various embodiments of the disclosure may have one or more of the following effects. The time-resolved fluorescent immunochromatographic test strip may detect PTX drugs with high detection sensitivity, high specificity, low production cost, and simple use. The test strip provided by the disclosure may be easy to manufacture and low in cost. The detection process may be simple and rapid. The PTX immunogen may have strong specificity and good immunogenicity. The prepared PTX antibody may have strong specificity, high titer, and no cross-reactivity with various PTX metabolites. The time-resolved fluorescence may have a large stock shift, which may reduce the interference of the specific stray light caused by the excitation light to the detection, which may improve the stability of the fluorescence detection. Some embodiments of the disclosure may not only have a long service life, but also eliminate the interference of the fluorescent substances in the environment to an object to be tested. Other embodiments of the time-resolved fluorescent immunochromatographic test strip may have wide excitation wavelength, narrow emission spectrum range, low background fluorescence intensity, and/or high resolution during the assay. Further embodiments of the time-resolved fluorescent immunochromatographic test strips and the HPLC are respectively used to measure PTX in human serum, and the results thereof are well fitted.

The foregoing descriptions are only exemplary implementation manners of the present invention. It should be noted that for a person of ordinary skill in the art, several improvements and modifications may further be made without departing from the principle of the present invention. These improvements and modifications should also be deemed as falling within the protection scope of the present invention.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various FIGURES need be carried out in the specific order described.

The disclosure claimed is:

1. A time-resolved fluorescent immunochromatographic test kit for detecting paclitaxel drugs, comprising a test paper and a sample diluent, wherein:

the test paper comprises a bottom plate and a sample absorption pad, a fluorescent microsphere pad, a bonding pad, and an absorbent pad which are sequentially overlapped on the bottom plate;

the fluorescent microsphere pad is sprayed with a fluorescent microsphere-labeled antipaclitaxel monoclonal antibody;

a detection area and a quality control area are immobilized on the bonding pad;

the detection area is sprayed with a paclitaxel hapten-carrier protein conjugate;

the quality control area is sprayed with a goat anti mouse antibody;

the anti-paclitaxel monoclonal antibody is prepared by using a paclitaxel hapten-carrier protein conjugate as an immunogen;

the paclitaxel hapten-carrier protein conjugate is obtained by coupling a 7-xylosyl paclitaxel hapten with a carrier protein; and the 7-xylosyl paclitaxel has the following formula:

wherein the anti-paclitaxel monoclonal antibody is expressed from a hybridoma deposited at the China General Microbiological Culture Collection Center (CGMCC) and the CGMCC number is 23027.

2. The time-resolved fluorescent immunochromatographic test kit for detecting paclitaxel drugs according to claim 1, wherein:

the fluorescent microsphere comprises rare earth ions $Eu^{3+}$ coated with polystyrene; and a surface of the microsphere contains a carboxyl group.

3. The time-resolved fluorescent immunochromatographic test kit for detecting paclitaxel drugs according to claim 2, wherein a diameter of the fluorescent microsphere is 100-300 nm.

4. The time-resolved fluorescent immunochromatographic test kit for detecting paclitaxel drugs according to claim 1, wherein:

the sample diluent is 0.008-0.012 mol/L of phosphate (PB) buffer;

a pH of the PB buffer is 7.2-7.6; and the PB buffer contains 0.15-0.25% (W/V) of 2 [4-(2,4,4-trimethylpentan-2-yl)phenoxy]ethanol.

5. A method for detecting paclitaxel drugs by a time-resolved fluorescent immunochromatographic test kit, comprising the steps of:

(1) pre-treating a sample with a sample diluent to obtain a sample to be tested;

(2) detecting the sample to be tested by using the time-resolved fluorescent immunochromatographic test kit to obtain a detected test kit; and (3) analyzing the detected test kit by a fluorescence detection analyzer to obtain a test result;

wherein:

the time-resolved fluorescent immunochromatographic test kit comprises a test paper and a sample diluent;

the test paper comprises a bottom plate and a sample absorption pad;

a fluorescent microsphere pad, a bonding pad, and an absorbent pad are sequentially overlapped on the bottom plate;

the fluorescent microsphere pad is sprayed with a fluorescent microsphere-labeled anti-paclitaxel monoclonal antibody;

a detection area and a quality control area are immobilized on the bonding pad;

the detection area is sprayed with a paclitaxel hapten-carrier protein conjugate;

the quality control area is sprayed with a goat anti mouse antibody;

the anti-paclitaxel monoclonal antibody is prepared by using a paclitaxel hapten-carrier protein conjugate as an immunogen;

the paclitaxel hapten-carrier protein conjugate is obtained by coupling a 7-xylosyl paclitaxel hapten with a carrier protein; and the 7-xylosyl paclitaxel has the following formula:
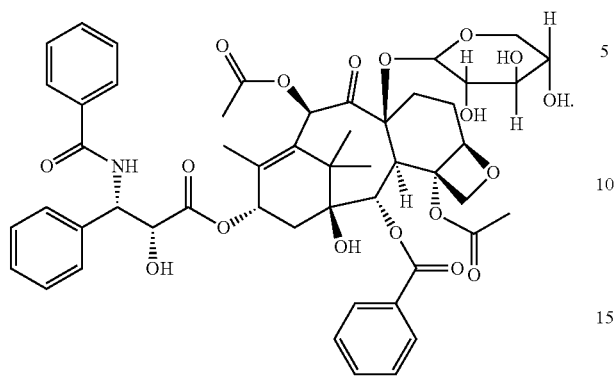
wherein the anti-paclitaxel monoclonal antibody is expressed from a hybridoma deposited at the China General Microbiological Culture Collection Center (CGMCC) and the CGMCC number is 23027.
* * * * *